(12) United States Patent
Tanba et al.

(10) Patent No.: US 10,274,389 B2
(45) Date of Patent: Apr. 30, 2019

(54) STORAGE MEDIUM, MATERIAL EVALUATING APPARATUS, AND MATERIAL EVALUATING METHOD

(71) Applicant: KYOCERA Document Solutions Inc., Osaka (JP)

(72) Inventors: Masato Tanba, Osaka (JP); Yoshitaka Matsuki, Osaka (JP); Yosuke Nakazato, Osaka (JP); Satoshi Kawakami, Osaka (JP); Wataru Endo, Osaka (JP)

(73) Assignee: KYOCERA Document Solutions Inc., Osaka (JP)

(*) Notice: Subject to any disclaimer, the term of this patent is extended or adjusted under 35 U.S.C. 154(b) by 965 days.

(21) Appl. No.: 14/470,245

(22) Filed: Aug. 27, 2014

(65) Prior Publication Data
US 2015/0066392 A1  Mar. 5, 2015

(30) Foreign Application Priority Data

Aug. 30, 2013 (JP) .................. 2013-180536
Aug. 30, 2013 (JP) .................. 2013-180539

(51) Int. Cl.
*G06K 9/00* (2006.01)
*G01L 19/08* (2006.01)
(Continued)

(52) U.S. Cl.
CPC .............. *G01L 19/08* (2013.01); *A61B 5/16* (2013.01); *G06K 9/00442* (2013.01); *A61B 5/7264* (2013.01)

(58) Field of Classification Search
CPC ......... A61B 5/16; A61B 5/7264; G01L 19/08; G01N 3/06
See application file for complete search history.

(56) References Cited

U.S. PATENT DOCUMENTS 7,024,022 B2   4/2006  Harrington et al.
7,035,438 B2   4/2006  Harrington et al.
(Continued)

FOREIGN PATENT DOCUMENTS

JP   H08-180037 A    7/1996
JP   2005-050351 A   2/2005
JP   2006-050494 A   2/2006

OTHER PUBLICATIONS

An Office Action; "Notice of Reasons for Rejection," issued by the Japanese Patent Office dated Nov. 10, 2015, which corresponds to Japanese Patent Application No. 2013-180539 and is related to U.S. Appl. No. 14/470,245.

(Continued)

*Primary Examiner* — Paul D Lee
*Assistant Examiner* — Mark I Crohn
(74) *Attorney, Agent, or Firm* — Studebaker & Brackett PC

(57) ABSTRACT

A non-transitory computer-readable storage medium has stored therein a material evaluating program. The material evaluating program includes a first program code and a second program code. The first program code causes a computer to evaluate, in units of pages included in a material, an object impression degree for each of all objects included in each of the pages, the object impression degree indicating the strength of an impression made by the object included in the page. The second program code causes the computer to display an evaluation result about the object impression degrees obtained by executing the first program code.

17 Claims, 9 Drawing Sheets

(51) Int. Cl.
*A61B 5/16* (2006.01)
*A61B 5/00* (2006.01)

(56) References Cited

U.S. PATENT DOCUMENTS

| | | |
|---|---|---|
| 7,035,439 B2 | 4/2006 | Harrington et al. |
| 7,072,495 B2 | 7/2006 | Harrington et al. |
| 7,092,551 B2 | 8/2006 | Harrington et al. |
| 7,092,552 B2 | 8/2006 | Harrington et al. |
| 7,095,877 B2 | 8/2006 | Harrington et al. |
| 7,116,802 B2 | 10/2006 | Harrington et al. |
| 7,130,450 B2 | 10/2006 | Harrington et al. |
| 7,130,451 B2 | 10/2006 | Harrington et al. |
| 7,136,511 B2 | 11/2006 | Harrington et al. |
| 2005/0028074 A1 | 2/2005 | Harrington et al. |
| 2005/0028075 A1 | 2/2005 | Harrington et al. |
| 2005/0028076 A1 | 2/2005 | Harrington et al. |
| 2005/0028096 A1 | 2/2005 | Harrington et al. |
| 2005/0028097 A1 | 2/2005 | Harrington et al. |
| 2005/0028098 A1 | 2/2005 | Harrington et al. |
| 2005/0028099 A1 | 2/2005 | Harrington et al. |
| 2006/0029258 A1 | 2/2006 | Harrington et al. |
| 2006/0029259 A1 | 2/2006 | Harrington et al. |
| 2006/0029260 A1 | 2/2006 | Harrington et al. |
| 2006/0039585 A1 | 2/2006 | Harrington et al. |

OTHER PUBLICATIONS

Ryo Takeshima et al., "Slide Revision Support System Using Impression-Based Interactive Summarization", FIT2013, 12th Forum on Information Technology 2013, Information Processing Society of Japan and The Institute of Electronics, Information and Communication Engineers, Aug. 20, 2013, vol. 4, No. M-023, pp. 369-370.

Keita Maeda et al, "Evaluation of Presentation Slides Based on Design Composition", Information Processing Society of Japan, Proceedings of 74th National Meeting, Mar. 6, 2012, vol. 4, No. 6ZG-5, pp. 4-861 to 4-862.

STORAGE MEDIUM, MATERIAL EVALUATING APPARATUS, AND MATERIAL EVALUATING METHOD

INCORPORATION BY REFERENCE

The present application claims priority under 35 U.S.C. § 119 to Japanese Patent Applications No. 2013-180536 and No. 2013-180539, both filed Aug. 30, 2013. The contents of this application are incorporated herein by reference in their entirety.

BACKGROUND

The present disclosure relates to a non-transitory computer-readable storage medium that has stored therein a material evaluating program for evaluating a material, a material evaluating apparatus for evaluating a material, and a material evaluating method for evaluating a material.

As a presentation material creation aiding system, a system that evaluates a material is known. Examples of known methods for evaluating a material include a method by which a degree of easiness-to-see of each of the objects in terms of the display configuration or layout is quantitatively evaluated based on the position of the object within the page.

SUMMARY

A non-transitory computer-readable storage medium according to an embodiment of the present disclosure has stored therein a material evaluating program to be executed by a computer. The material evaluating program includes a first program code and a second program code. The first program code causes the computer to evaluate, in units of pages included in a material, an object impression degree for each of all objects included in each of the pages, the object impression degree indicating the strength of an impression made by the object included in the page. The second program code causes the computer to display an evaluation result obtained by executing the first program code.

A material evaluating apparatus according to an embodiment of the present disclosure includes: an object impression degree evaluating section, a display, and an evaluation displaying section. The object impression degree evaluating section evaluates, in units of pages included in a material, an object impression degree for each of all objects included in each of the pages, the object impression degree indicating the strength of an impression made by the object included in the page. The evaluation displaying section causes the display to display an evaluation result obtained by the object impression degree evaluating section.

A material evaluating method according to an embodiment of the present disclosure includes: evaluating, via an object impression degree evaluating section and in units of pages included in a material, an object impression degree for each of all objects included in each of the pages, the object impression degree indicating the strength of an impression made by the object included in the page. The material evaluating method according to the embodiment of the present disclosure further includes: causing, via an evaluation displaying section, a display to display an evaluation result obtained by the object impression degree evaluating section.

DETAILED DESCRIPTION

Figure 1:
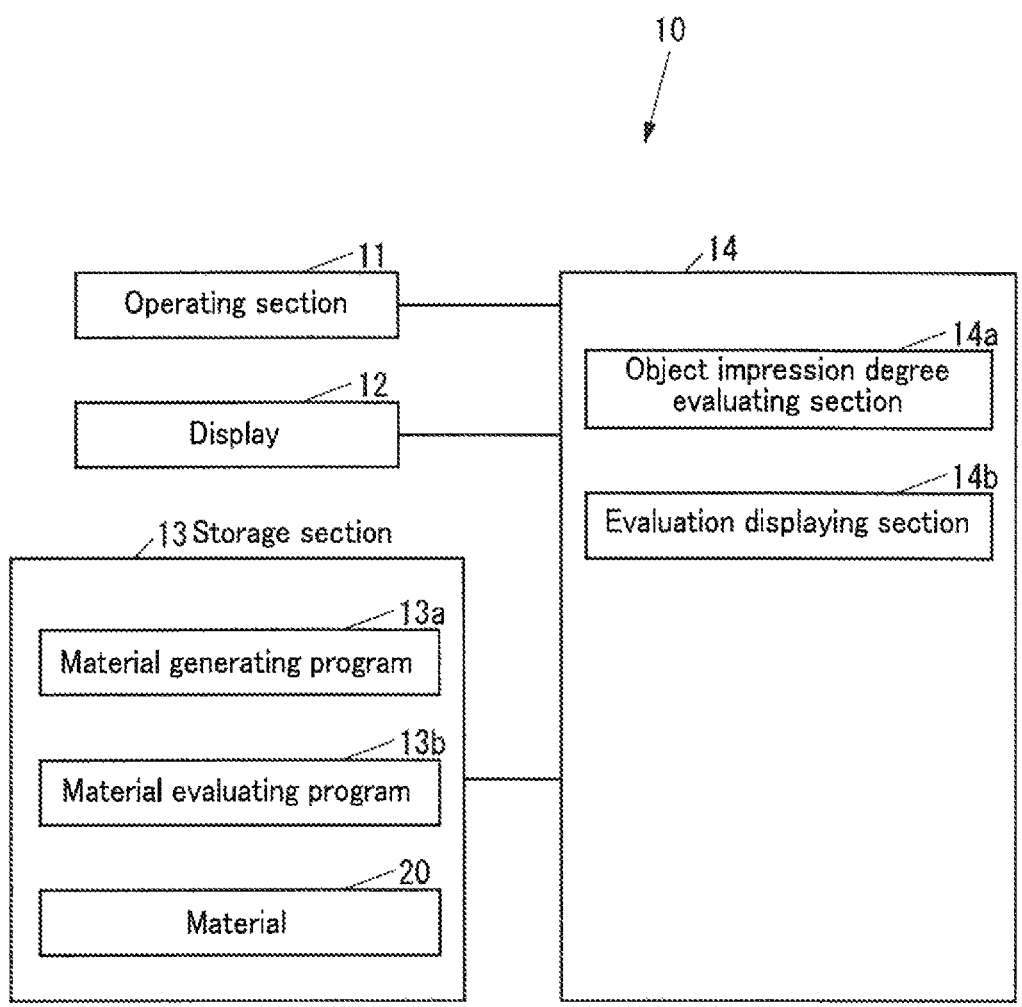
FIG. 1 shows a configuration of a material evaluating apparatus according to a first embodiment of the present disclosure.

The following describes embodiments of the present disclosure with reference to the drawings. Some of the items shown in the drawings that are either the same or corresponding will be referred to by using the same reference characters, and explanation thereof will not be duplicated.

First Embodiment

A first embodiment of the present disclosure will be explained below, with reference to drawings.

First, a configuration of a material evaluating apparatus according to the first embodiment will be explained.

FIG. 1 shows the configuration of the material evaluating apparatus according to the first embodiment.

As shown in FIG. 1, a material evaluating apparatus 10 includes an operating section 11, a display 12, a storage section 13, and a controlling section 14. The operating section 11 may be an input device to which various types of operations are input. The operating section 11 may be configured with a mouse, a keyboard, or the like. The display 12 may be a display device that displays various types of information. The display 12 may be configured with a Liquid Crystal Display (LCD) device or the like. The storage section 13 is a device that stores therein one or more computer programs (hereinafter, "programs") and various types of data. A non-volatile memory (a storage medium) such as a Hard Disk Drive (HDD) may be used as the storage section 13. The controlling section 14 controls the entirety of the material evaluating apparatus 10. The material evaluating apparatus 10 is configured with a computer such as a Personal Computer (PC).

The storage section 13 is capable of storing therein a material 20 generated by the controlling section 14.

Figure 2:
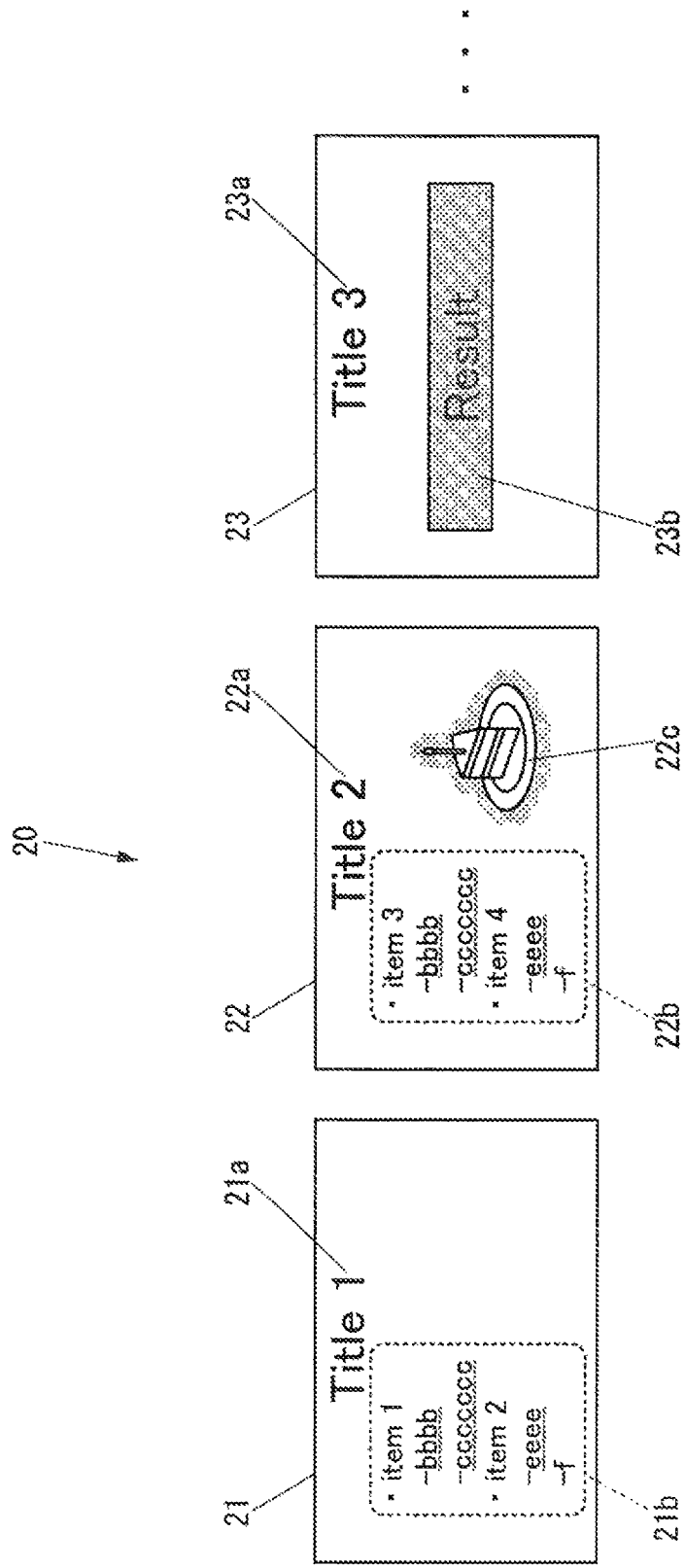
FIG. 2 shows an example of a material according to embodiments of the present disclosure.

FIG. 2 shows an example of the material 20.

As shown in FIG. 2, the material 20 may include a plurality of slides each of which is a page. For example, the material 20 may include slides 21, 22, and 23. The slide 21 includes an object 21a and an object 21b. The slide 22 includes an object 22a, an object 22b, and an object 22c. The slide 23 includes an object 23a and an object 23b. The objects 21a, 21b, 22a, 22b, 23a and 23b are each a character string object. The object 22c is an image object.

The controlling section 14 is capable of generating the material 20 with various contents in accordance with purposes thereof. Examples of the material 20 include a presentation material to be used in a presentation.

As shown in FIG. 1, the storage section 13 has stored therein a material generating program 13a used for generating the material 20. Further, the storage section 13 has stored therein a material evaluating program 13b used for evaluating the material 20. The material generating program 13a and the material evaluating program 13b may be installed in the material evaluating apparatus 10 at a manufacturing stage of the material evaluating apparatus 10. Alternatively, the material generating program 13a and the material evaluating program 13b may additionally be installed in the material evaluating apparatus 10 from a storage medium such as a Compact Disk (CD), a Digital Versatile Disk (DVD), or the like. In another example, the material generating program 13a and the material evaluating program 13b may additionally be installed in the material evaluating apparatus 10 via a network.

The controlling section 14 includes, for example, a Central Processing Unit (CPU), a Read-Only Memory (ROM), and a Random Access Memory (RAM). The ROM is a storage medium that stores therein one or more programs and various types of data. The RAM is used as a working area of the CPU. The CPU executes any of the programs stored in the ROM and the storage section 13.

The controlling section 14 functions as an object impression degree evaluating section 14a and an evaluation displaying section 14b, by executing the material evaluating program 13b stored in the storage section 13. The object impression degree evaluating section 14a evaluates, in units of objects, a degree of impression made by each object (hereinafter, "object impression degree") for each of all the objects included in each of the slides (the pages). In other words, the object impression degree is evaluated for each of all the objects included in each slide. The object impression degree indicates the strength of an impression made by each object. The evaluation displaying section 14b causes the display 12 to display an evaluation result obtained by the object impression degree evaluating section 14a.

Next, operations performed by the material evaluating apparatus 10 will be explained.

First, an operation performed by the material evaluating apparatus 10 to generate the material 20 will be explained.

The controlling section 14 included in the material evaluating apparatus 10 generates the material 20 corresponding to an operation input to the operating section 11, by executing the material generating program 13a stored in the storage section 13.

Next, operations performed by the material evaluating apparatus 10 to evaluate the material 20 will be explained.

The controlling section 14 included in the material evaluating apparatus 10 evaluates uniformity of the slides included in the material 20 by executing the material evaluating program 13b stored in the storage section 13. Further, the controlling section 14 included in the material evaluating apparatus 10 evaluates the object impression degrees by executing the material evaluating program 13b stored in the storage section 13.

First, an operation performed by the material evaluating apparatus 10 to evaluate the uniformity of the slides included in the material 20 will be explained.

Figure 3:
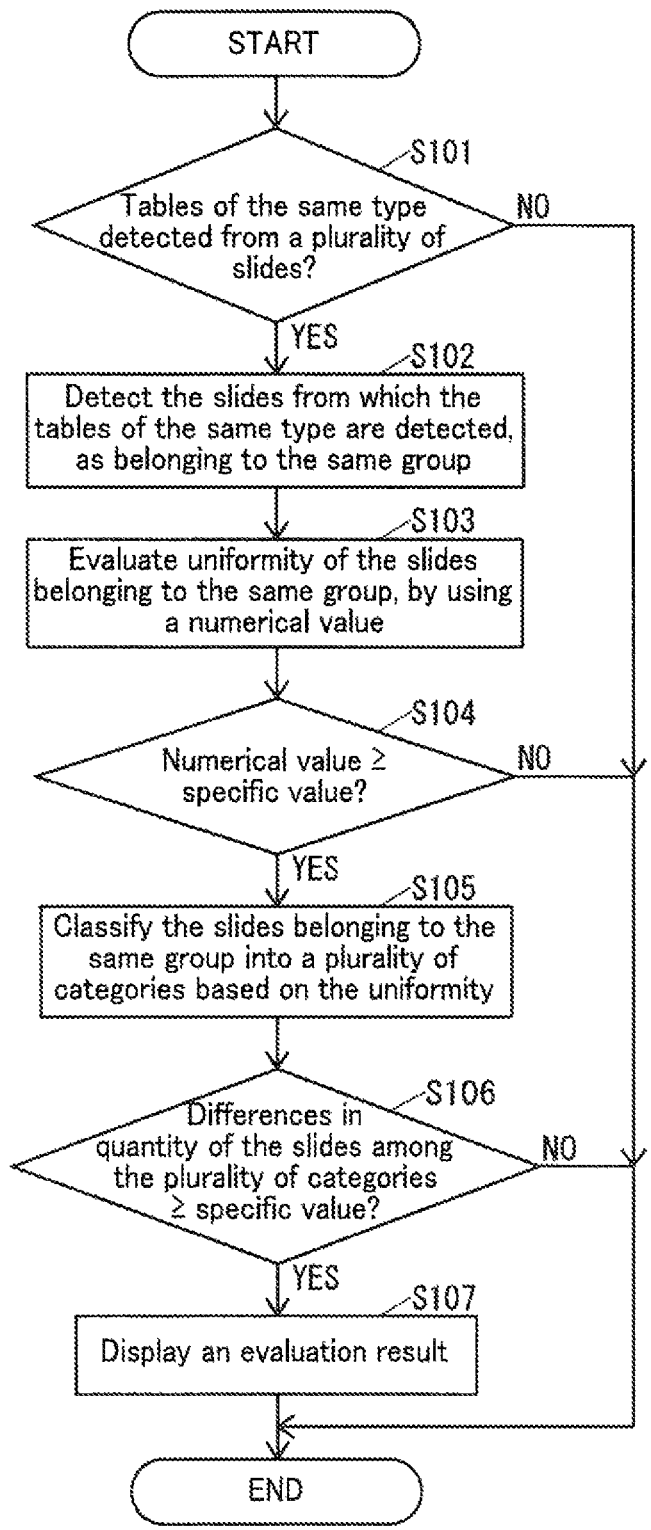
FIG. 3 shows an operation performed by the material evaluating apparatus to evaluate uniformity of slides according to the first embodiment of the present disclosure.

The controlling section 14 performs the operation shown in FIG. 3 in accordance with an operation input to the operating section 11.

FIG. 3 shows the operation performed by the material evaluating apparatus 10 to evaluate the uniformity of the slides included in the material 20.

As shown in FIG. 3, the controlling section 14 judges whether the targeted material 20 includes a plurality of slides from which tables of mutually the same type are detected (step S101). For example, if the headings of a plurality of tables are the same as one another, the controlling section 14 determines that these tables are of mutually the same type.

If the controlling section 14 has determined that the targeted material 20 does not include a plurality of slides from which tables of mutually the same type are detected (step S101: No), the operation shown in FIG. 3 is ended.

On the contrary, if the controlling section 14 has determined that the targeted material 20 includes a plurality of slides from which tables of mutually the same type are detected (step S101: Yes), the controlling section 14 detects these slides as slides belonging to mutually the same group (step S102).

Subsequently, the controlling section 14 evaluates uniformity of the detected plurality of slides belonging to mutually the same group by using a numerical value (step S103).

For example, in step S103, the controlling section 14 evaluates the uniformity of the plurality of slides belonging to mutually the same group, from an aspect of positions, within the slides, of the tables of mutually the same type included in the respective slides. In other words, the controlling section 14 evaluates the uniformity of the slides by using a numerical value, by expressing with the numerical value (hereinafter "quantifying") the differences in the positions of the tables of mutually the same type within the slides according to a specific rule.

In another example, in step S103, the controlling section 14 evaluates the uniformity of the plurality of slides belonging to mutually the same group, from an aspect of sizes of the tables of mutually the same type included in the respective slides. In other words, the controlling section 14 evaluates the uniformity of the slides by using a numerical value, by quantifying the differences in the sizes of the tables of mutually the same type according to a specific rule.

In yet another example, in step S103, the controlling section 14 evaluates the uniformity of the plurality of slides belonging to mutually the same group, from an aspect of colors of the tables of mutually the same type included in the respective slides. In other words, the controlling section 14 evaluates the uniformity of the slides by using a numerical value, by quantifying color differences among the tables of mutually the same type according to a specific rule.

In yet another example, in step S103, the controlling section 14 evaluates the uniformity of the slides, from an aspect of the background color of each of the plurality of slides belonging to mutually the same group. In other words, the controlling section 14 evaluates the uniformity of the slides by using a numerical value, by quantifying color differences of the backgrounds among the slides according to a specific rule.

In yet another example, in step S103, the controlling section 14 evaluates the uniformity of the plurality of slides belonging to mutually the same group, from each of the various aspects described above. In other words, the controlling section 14 realizes the quantification process, from two or more of the various aspects that are: the aspect of the positions of the tables of mutually the same type included in the slides; the aspect of the sizes of the tables of mutually the same type included in the slides; the aspect of the colors of the tables of mutually the same type included in the slides; and the aspect of the background colors of the slides.

After the process in step S103, the evaluation displaying section 14b judges whether the numerical value indicating the uniformity of the plurality of slides belonging to mutually the same group is equal to or larger than a specific value (step S104). When the quantification process was performed with respect to two or more aspects, the evaluation displaying section 14b makes the judgment for each of the aspects.

If the evaluation displaying section 14b has determined that the numerical value indicating the uniformity is not equal to or larger than the specific value (step S104: No), the controlling section 14 ends the operation shown in FIG. 3. When the quantification process was performed with respect to two or more aspects, the controlling section 14 ends the operation shown in FIG. 3, if the numerical value indicating the uniformity is not equal to or larger than the specific value for any of the aspects.

On the contrary, upon determining that the numerical value indicating the uniformity is equal to or larger than the specific value (step S104: Yes), the evaluation displaying section 14b classifies the plurality of slides belonging to mutually the same group detected in step S102 into a plurality of categories based on the uniformity (step S105). For example, when the uniformity of the plurality of slides belonging to mutually the same group is evaluated from the aspect of the background colors of the slides, if the numerical value indicating the uniformity is equal to or larger than the specific value, it means that there are two or more background colors. Thus, in that situation, the evaluation displaying section 14b divides the plurality of slides belonging to mutually the same group according to the background colors thereof (i.e., classifies the slides into the plurality of categories). Further, when it has been determined that the numerical value indicating the uniformity is equal to or larger than the specific value with respect to two or more aspects, the plurality of slides belonging to mutually the same group are classified into a plurality of categories, for each of the aspects.

Subsequently, the evaluation displaying section 14b judges whether any of the differences in quantity of the slides among the classified plurality of categories is equal to or larger than a specific value (step S106). When the plurality of slides belonging to mutually the same group are classified into the plurality of categories with respect to two or more aspects, the evaluation displaying section 14b makes the judgment for each of the aspects.

If the evaluation displaying section 14b has determined that none of the differences in quantity of the slides among the classified plurality of categories is equal to or larger than the specific value (step S106: No), the controlling section 14 ends the operation shown in FIG. 3. When the plurality of slides belonging to mutually the same group are classified into the plurality of categories with respect to two or more aspects, the controlling section 14 ends the operation shown in FIG. 3 if it has been determined that none of the differences in quantity of the slides among the classified plurality of categories is equal to or larger than the specific value for every aspect.

On the contrary, if the evaluation displaying section 14b has determined that at least one of the differences in quantity of the slides among the classified plurality of categories is equal to or larger than the specific value (step S106: Yes), the evaluation displaying section 14b causes the display 12 to display the evaluation result obtained in step S103 (step S107). When the plurality of slides belonging to mutually the same group are classified into the plurality of categories with respect to two or more aspects, the display 12 is caused to display at least one evaluation result, if it has been determined that at least one of the differences in quantity of the slides among the classified plurality of categories is equal to or larger than the specific value with respect to at least one of the aspects. After that, in response to an instruction input via the operating section 11 to end the display of the evaluation result, the controlling section 14 ends the operation shown in FIG. 3.

Figure 4:
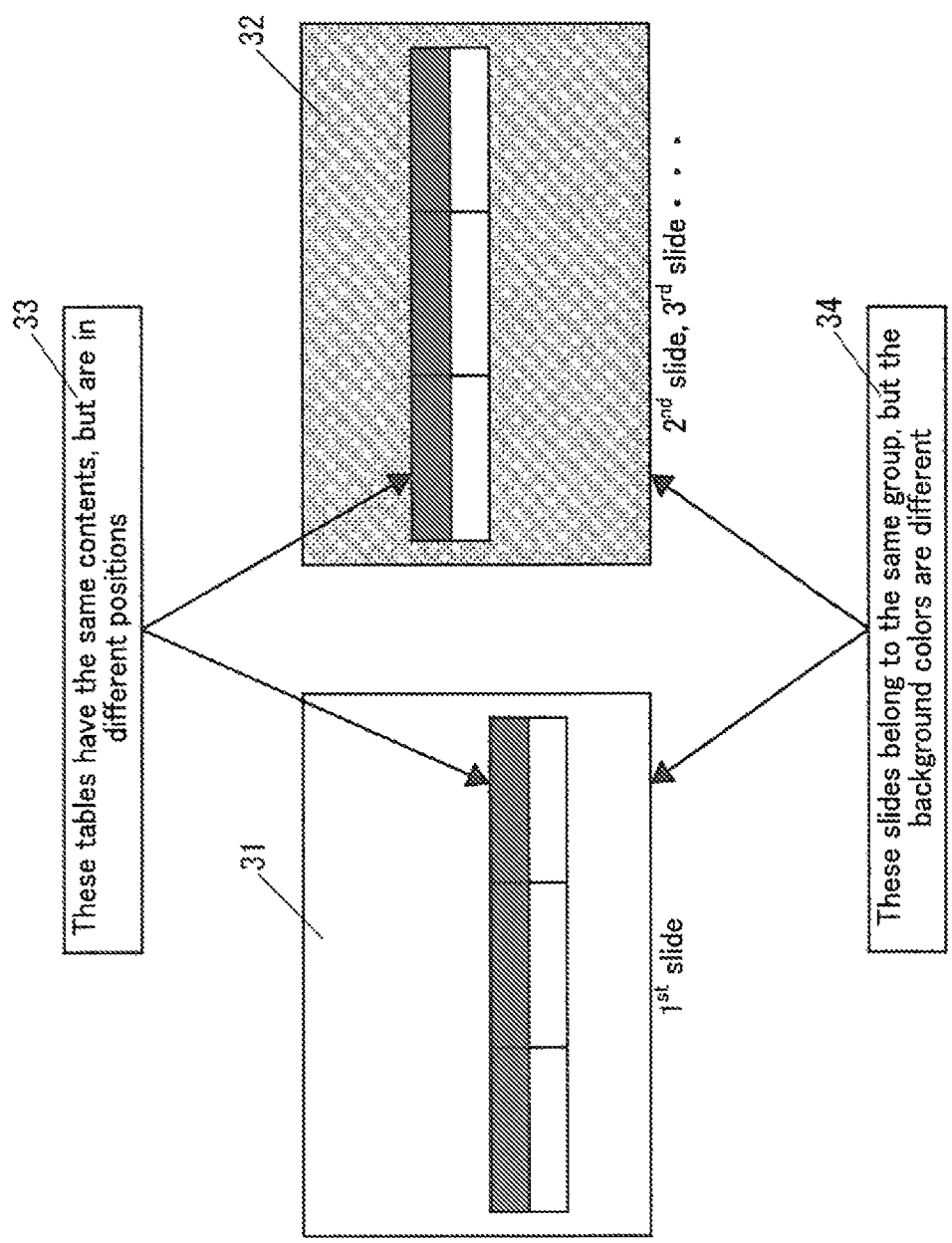
FIG. 4 shows examples of evaluation results about the uniformity of the slides according to the first embodiment of the present disclosure.

FIG. 4 shows examples of evaluation results about the uniformity that are displayed by the display 12.

FIG. 4 shows the evaluation results about a material 20 that is different from the material 20 shown in FIG. 2. In the evaluation results shown in FIG. 4, an image 31 is a schematic representation of the first slide included in the material 20. Further, an image 32 is a schematic representation of each of the second, the third, . . . slides included in the material 20. Of the plurality of categories classified in step S105, the image 31 represents a category having the smaller quantity of slides (i.e., the category of slides in the minority). Of the plurality of categories classified in step S105, the image 32 represents a category having the larger quantity of slides (i.e., the category of slides in the majority).

A message 33 indicates that the positions, within the slides, of the tables of mutually the same type included in the plurality of slides belonging to mutually the same group are not uniform. A message 34 indicates that the background colors of the plurality of slides belonging to mutually the same group are not uniform.

Next, an operation (a material evaluating method) performed by the material evaluating apparatus 10 to evaluate the object impression degrees will be explained.

Figure 5:
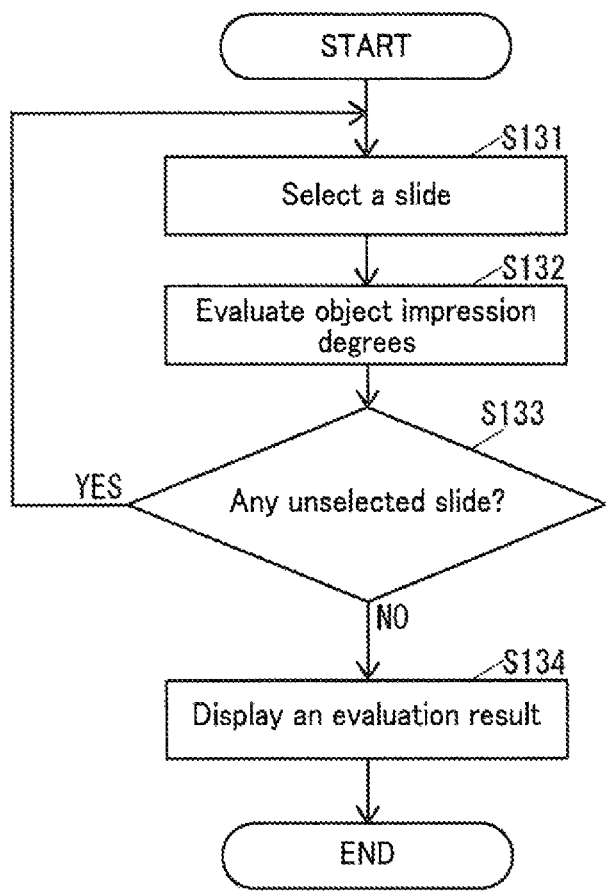
FIG. 5 shows an operation performed by the material evaluating apparatus to evaluate object impression degrees according to the first embodiment of the present disclosure.

The controlling section 14 performs the operation shown in FIG. 5 in accordance with an operation input to the operating section 11.

FIG. 5 shows the operation performed by the material evaluating apparatus 10 to evaluate the object impression degrees. By executing a first program code included in the material evaluating program 13b, the controlling section 14 functions as the object impression degree evaluating section 14a. Further, by executing a second program code included in the material evaluating program 13b, the controlling section 14 functions as the evaluation displaying section 14b that causes the display 12 to display an evaluation result obtained by the object impression degree evaluating section 14a.

As shown in FIG. 5, the object impression degree evaluating section 14a selects one of the plurality of slides included in a targeted material 20 (step S131). While the process of evaluating the object impression degrees is being performed, the plurality of slides included in the material 20 are sequentially selected, starting with the first slide. In other words, the object impression degrees are evaluated in units of slides (i.e., in units of pages).

Subsequently, the object impression degree evaluating section 14a evaluates an object impression degree for each of all the objects included in the selected slide (step S132). The object impression degrees each indicate the strength of an impression made by the object, in units of objects.

For example, in step S132, the object impression degree evaluating section 14a evaluates the object impression degrees based on the types of the objects. In other words, the object impression degree evaluating section 14a evaluates each of the object impression degrees by using a numerical value, by quantifying the type of the object according to a specific rule. For example, when the type of an object is an image, the object impression degree evaluating section 14a arranges the object impression degree of the object being an image to be higher than the object impression degree of an object of which the type is a character string. In other words, the object impression degree of the image object is higher than that of the character string object.

In another example, in step S132, the object impression degree evaluating section 14a evaluates the object impression degrees based on the position of each of the objects in the selected slide. In other words, the object impression degree evaluating section 14a evaluates each of the object impression degrees by using a numerical value, by quantifying the position of the object within the slide according to a specific rule. For example, the object impression degree evaluating section 14a determines such that the object impression degree of an object is higher (the numerical value is larger) as the position of the object in the slide is higher. Further, the object impression degree evaluating section 14a determines such that the object impression degree of an object is higher (the numerical value is larger) as the position of the object in the slide is closer to the center in terms of the left-and-right direction.

In yet another example, in step S132, the object impression degree evaluating section 14a evaluates the object impression degrees based on the size of each of the objects. In other words, the object impression degree evaluating section 14a evaluates each of the object impression degrees by using a numerical value, by quantifying the size of the object according to a specific rule. For example, the object impression degree evaluating section 14a determines such that the object impression degree of an object is higher (the numerical value is larger) as the object is larger in size.

In yet another example, in step S132, the object impression degree evaluating section 14a evaluates the object impression degrees based on the magnitude of a color difference between the background of the selected slide and each of the objects. In other words, the object impression degree evaluating section 14a evaluates each of the object impression degrees by using a numerical value, by quantifying the magnitude of the color difference between the object and the background of the slide according to a specific rule. For example, the object impression degree evaluating section 14a determines such that the object impression degree of an object is higher (the numerical value is larger) as the magnitude of the color difference between the object and the background of the slide is larger.

In yet another example, in step S132, the object impression degree evaluating section 14a evaluates the object impression degrees based on the magnitude of color differences among the plurality of objects included in the selected slide. In other words, the object impression degree evaluating section 14a evaluates each of the object impression degrees by using a numerical value, by quantifying the magnitude of the color differences among the plurality of objects according to a specific rule. For example, when the selected slide includes three objects A, B, and C having mutually different colors, the object impression degree evaluating section 14a evaluates an object impression degree of the object A, by adding together a numerical value based on the magnitude of a color difference between the object A and the object B and a numerical value based on the magnitude of a color difference between the object A and the object C. Similarly, the object impression degree evaluating section 14a evaluates an object impression degree of the object B, by adding together a numerical value based on the magnitude of the color difference between the object B and the object A and a numerical value based on the magnitude of a color difference between the object B and the object C. Also similarly, the object impression degree evaluating section 14a evaluates an object impression degree of the object C, by adding together a numerical value based on the magnitude of the color difference between the object C and the object A and a numerical value based on the magnitude of the color difference between the object C and the object B. The object impression degree evaluating section 14a may determine such that the object impression degree of an object is higher (the numerical value is larger) as the magnitude of the color difference is larger. Alternatively, of the objects included in the selected slide, the object impression degree evaluating section 14a may arrange the object impression degree to be higher (to have a larger numerical value) only for the object having the largest color difference from the slide background.

In yet another example, in step S132, if the type of an object is a character string, the object impression degree evaluating section 14a evaluates the object impression degree based on the text size of the character string. In other words, if the type of an object is a character string, the object impression degree evaluating section 14a evaluates the object impression degree by using a numerical value, by quantifying the text size of the character string according to a specific rule. For example, the object impression degree evaluating section 14a determines such that the object impression degree of an object is higher (the numerical value is larger) as the text size of a character string is larger.

In yet another example, in step S132, if the type of an object is a character string, the object impression degree evaluating section 14a evaluates the object impression degree based on the quantity of characters in the character string. In other words, if the type of an object is a character string, the object impression degree evaluating section 14a evaluates the object impression degree by using a numerical value, by quantifying the quantity of characters in the character string according to a specific rule. For example, the object impression degree evaluating section 14a determines such that the object impression degree of an object is higher (the numerical value is larger) as the quantity of characters in the character string is smaller.

In yet another example, in step S132, the object impression degree evaluating section 14a evaluates an object impression degree of each of the objects comprehensively by using a numerical value, by performing a quantification process on each of all the objects included in the selected slide from each of the various aspects described above and totaling the obtained numerical values in units of objects. In other words, the object impression degree evaluating section 14a evaluates each of the object impression degrees by using the numerical value, by performing the quantification process from two or more of the various aspects and adding together the obtained numerical values from those aspects to calculate a total object impression degree. As described above, the various aspects are: the aspect of the type of the object; the aspect of the position of the object; the aspect of the size of the object; the aspect of the color difference between the background of the selected slide and the object; the aspect of the color differences among the plurality of objects; the aspect of the text size of the character string; and the aspect of the quantity of characters in the character string.

After that, the object impression degree evaluating section 14a judges whether there is any slide that has not been selected (step S133). If the object impression degree evaluating section 14a has determined that there are one or more unselected slides, the process returns to step S131. Until the process of evaluating the object impression degrees is performed on each of all the slides included in the targeted material 20, the process in steps S131 through S133 is repeatedly performed.

If the object impression degree evaluating section 14a has determined that there is no unselected slide, the evaluation displaying section 14b causes the display 12 to display an evaluation result about the object impression degrees (step S134). After that, in response to an instruction input via the operating section 11 to end the display of the evaluation result, the controlling section 14 ends the operation shown in FIG. 5.

Figure 6:
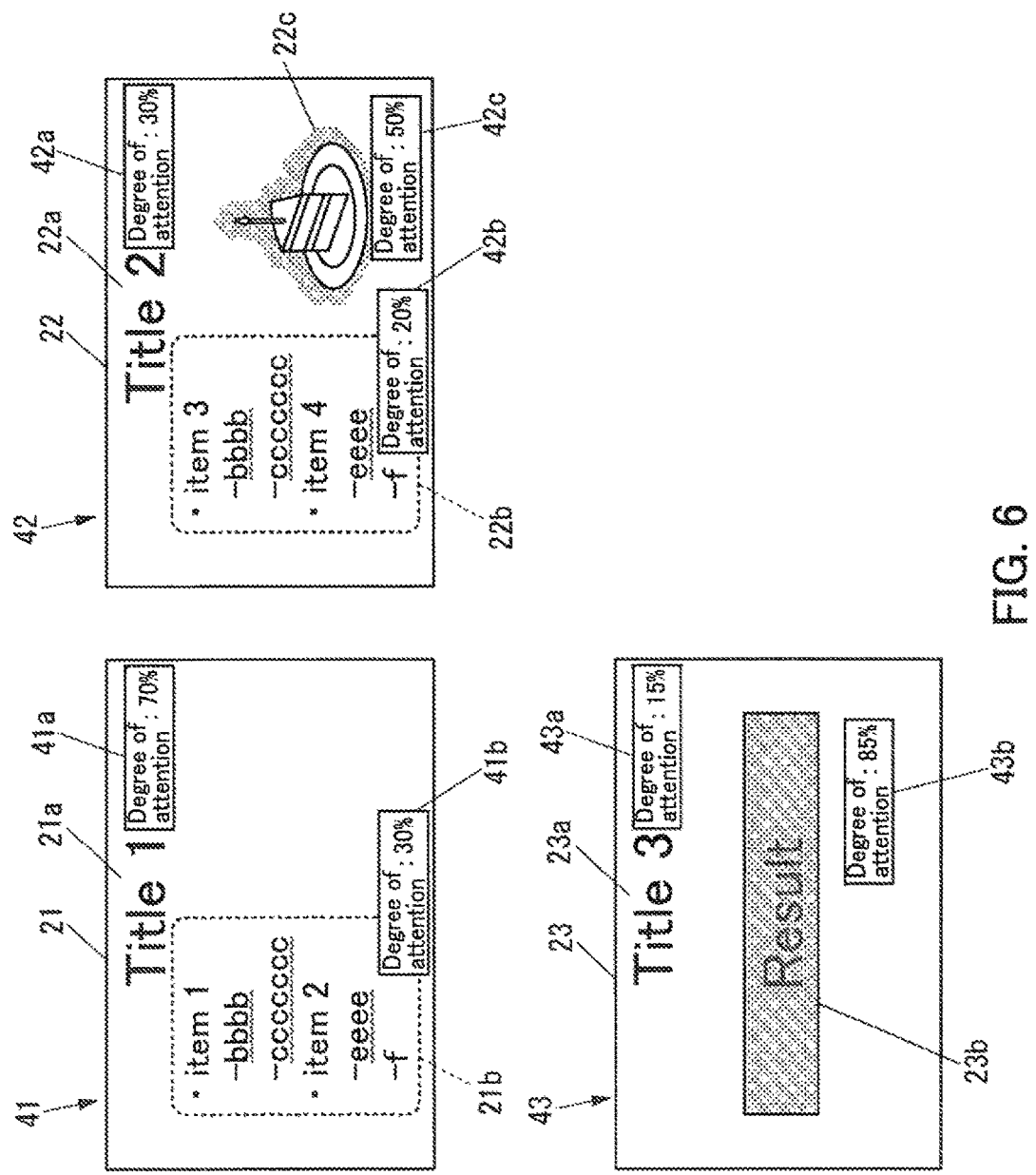
FIG. 6 shows examples of evaluation results about the object impression degrees according to the first embodiment of the present disclosure.

FIG. 6 shows examples of evaluation results about the object impression degrees that are displayed on the display 12. More specifically, FIG. 6 shows evaluation results for the material 20 shown in FIG. 2.

In the evaluation results shown in FIG. 6, an image 41 represents the slide 21. A message 41a indicates a 70% degree of attention (i.e., a degree of attention attracted by the object) as an object impression degree of the object 21a. A message 41b indicates a 30% degree of attention as an object impression degree of the object 21b.

Further, an image 42 represents the slide 22. A message 42a indicates a 30% degree of attention as an object impression degree of the object 22a. A message 42b indicates a 20% degree of attention as an object impression degree of the object 22b. A message 42c indicates a 50% degree of attention as an object impression degree of the object 22c.

Further, an image 43 represents the slide 23. A message 43a indicates a 15% degree of attention as an object impression degree of the object 23a. A message 43b indicates an 85% degree of attention as an object impression degree of the object 23b.

The evaluation results shown in FIG. 6 indicate the object impression degrees with the percentage values, in such a manner that the sum of the object impression degree values of all the objects included in each of the slides 21, 22, and 23 is equal to 100%. However, as long as it is possible to express a relative relationship among the strengths of the impressions made by all the objects included in each of the slides, the evaluation results do not necessarily have to be expressed with percentage values. For example, it is acceptable to show the numerical values indicating the object impression degrees obtained in step S132, without any conversion. When the object impression degrees are quantified from two or more aspects, values (total values) each obtained by adding together the numerical values from the two or more aspects may be shown.

FIG. 6 indicates an example in which the display 12 displays the evaluation results for the three slides (i.e., the slides 21, 22, and 23) at the same time. However, the quantity of slides displayed on the display 12 at the time of an evaluation of the object impression degrees is not limited to three. For example, the slides may be displayed one by one.

As explained above, the material evaluating apparatus 10 evaluates the object impression degree for each of all the objects included in the slides (step S132) and displays the evaluation result (step S134). Accordingly, the material evaluating apparatus 10 is able to help the user recognize objectively which object makes a strong impression in each of the slides included in the material 20.

For instance, in the example shown in FIG. 6, the slide 22 has the image object 22c added thereto, in contrast to the slide 21. Embedding an image object for the purpose of filling an empty space is an often-used method. However, if the object impression degree of the object 22c is evaluated as high because the colors used in the image object 22c are vivid, for example, the object impression degree of the character string object 22b happens to be evaluated as low, relative to the object 22c. In that situation, if the contents of the object 22b are important, the slide 22 shown in FIG. 6 may be revised.

The material evaluating apparatus 10 is able to help the user recognize appropriate evaluation results of the object impression degrees that are based on at least one of the following: the type of the object; the position of the object within the slide; the size of the object; the color differences among all the objects within each slide; the color difference between the object and the background of the slide; the text size of the character string when the type of the object is a character string; and the quantity of characters when the type of the object is a character string.

An object having a large color difference from the background of the slide usually makes a strong impression. Thus, the material evaluating apparatus 10 evaluates the object impression degree of an object having a large color difference from the slide background as high. As a result, the material evaluating apparatus 10 is able to help the user recognize an appropriate evaluation result.

As another example, an object having large color differences from other objects in the slide usually makes a strong impression. Thus, the material evaluating apparatus 10 evaluates the object impression degree of an object having large color differences from other objects as high. As a result, the material evaluating apparatus 10 is able to help the user recognize an appropriate evaluation result.

An image object usually makes a stronger impression than a character string object does. Thus, the material evaluating apparatus 10 evaluates the object impression degree of an image object as higher than the object impression degree of a character string object. As a result, the material evaluating apparatus 10 is able to help the user recognize an appropriate evaluation result.

Further, when a plurality of image objects overlap one another, the material evaluating apparatus 10 may evaluate the object impression degrees of those objects as low. By acknowledging the object impression degrees displayed by the material evaluating apparatus 10, the user of the material evaluating apparatus 10 is able to immediately recognize the part that is difficult to visually perceive due to the overlapping of the plurality of image objects.

By acknowledging the objective evaluation result about the object impression degrees displayed by the material evaluating apparatus 10, the person who generated the material 20 (hereinafter, "creator") is able to objectively recognize if a part of the slide where he/she desires the impression to be strong makes a strong impression as desired. As a result, the creator of the material 20 is able to appropriately revise the material 20 in a short period of time.

Second Embodiment

Next, a second embodiment of the present disclosure will be explained, with reference to drawings. Some of the items that are the same as those described in the first embodiment will not be explained in detail. Only the items that are different from those described in the first embodiment will be explained in detail.

Figure 7:
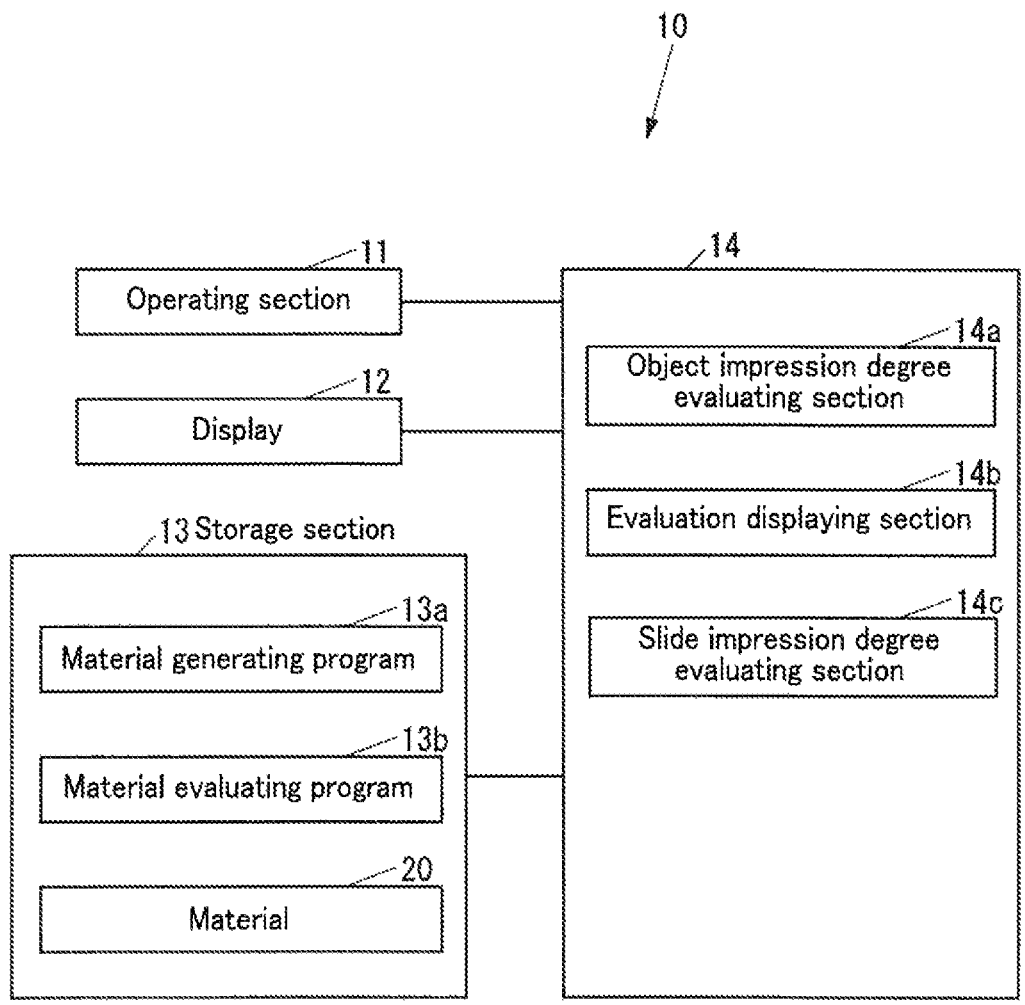
FIG. 7 shows a configuration of a material evaluating apparatus according to a second embodiment of the present disclosure.

First, a configuration of a material evaluating apparatus according to the second embodiment will be explained. FIG. 7 shows the configuration of the material evaluating apparatus according to the second embodiment.

As shown in FIG. 7, the material evaluating apparatus 10 includes the operating section 11, the display 12, the storage section 13, and the controlling section 14. The controlling section 14 functions as the object impression degree evaluating section 14a, the evaluation displaying section 14b, and a slide impression degree evaluating section 14c, by executing the material evaluating program 13b stored in the storage section 13.

The slide impression degree evaluating section 14c evaluates, in units of slides, a degree of impression made by each slide (hereinafter, "slide impression degree (page impression degree)") for the slides (the pages) included in a material. In other words, when a material includes a plurality of slides, the slide impression degree is evaluated for each of all the slides included in the material. The slide impression degree indicates the strength of an impression made by each slide (each page).

Like in the first embodiment, the evaluation displaying section 14b has the function of causing the display 12 to display an evaluation result obtained by the object impression degree evaluating section 14a, when the process of evaluating the object impression degrees has been performed. In addition, the evaluation displaying section 14b further has a function of causing the display 12 to display an evaluation result obtained by the slide impression degree evaluating section 14c, when the process of evaluating the slide impression degrees has been performed.

Next, an operation performed by the material evaluating apparatus 10 to evaluate the material 20 will be explained.

Like in the first embodiment, the controlling section 14 included in the material evaluating apparatus 10 is able to evaluate the uniformity of the slides in the material 20 by executing the material evaluating program 13b stored in the storage section 13. Further, like in the first embodiment, the controlling section 14 included in the material evaluating apparatus 10 is able to evaluate the object impression degrees by executing the material evaluating program 13b stored in the storage section 13. In addition, the controlling section 14 included in the material evaluating apparatus 10 is able to evaluate the slide impression degrees by executing the material evaluating program 13b stored in the storage section 13.

The following will describe an operation (a material evaluating method) performed by the material evaluating apparatus 10 to evaluate the slide impression degrees. The material evaluating apparatus 10 relatively evaluates the strength of an impression made by each of the plurality of slides included in the material 20.

Figure 8:
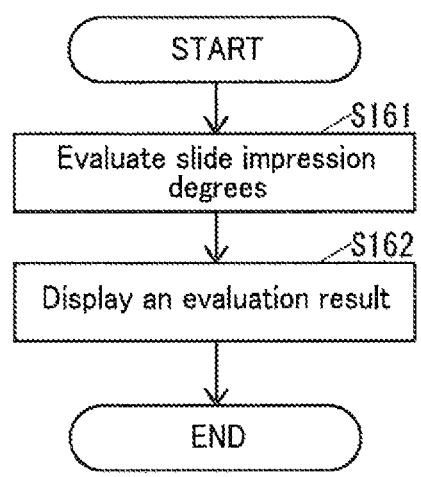
FIG. 8 shows an operation performed by the material evaluating apparatus according to the second embodiment of the present disclosure.

The controlling section 14 performs the operation shown in FIG. 8 in accordance with an operation input to the operating section 11.

FIG. 8 shows the operation performed by the material evaluating apparatus 10 to evaluate the slide impression degrees. The controlling section 14 functions as the slide impression degree evaluating section 14c by executing a third program code included in the material evaluating program 13b. Further, the controlling section 14 functions as the evaluation displaying section 14b that causes the display 12 to display an evaluation result obtained by the slide impression degree evaluating section 14c by executing a fourth program code included in the material evaluating program 13b.

As shown in FIG. 8, the slide impression degree evaluating section 14c evaluates a slide impression degree for each of all the slides included in a targeted material 20 (step S161).

For example, in step S161, the slide impression degree evaluating section 14c evaluates the slide impression degree of each of the slides, based on the degree of difference in the slide appearance from an appearance tendency of the slides in the entirety of the material 20. In other words, the slide impression degree evaluating section 14c evaluates the slide impression degree of each of the slides by using a numerical value, by quantifying the degree of difference in the slide appearance from the appearance tendency of the slides in the entirety of the material 20 according to a specific rule. For example, the slide impression degree evaluating section 14c determines such that the slide impression degree of a slide is higher (the numerical value is larger) as the degree of difference from the appearance tendency of the slides in the entirety of the material 20 is higher.

Alternatively, the slide impression degree evaluating section 14c may evaluate the slide impression degree of each of the slides, based on the degree of difference in the slide appearance from the appearance tendency of the slides in the entirety of the material 20 and the maximum value among the object impression degrees in the slide. In other words, the slide impression degree evaluating section 14c quantifies the degree of difference in the slide appearance from the appearance tendency of the slides in the entirety of material 20 according to a specific rule. In addition, the object impression degree evaluating section 14a evaluates the object impression degree for each of all the objects included in each of the slides by using a numerical value. Further, the slide impression degree evaluating section 14c obtains the maximum value among the object impression degrees for each of the slides, by referring to the evaluation results obtained by the object impression degree evaluating section 14a. For example, the slide impression degree evaluating section 14c determines such that the slide impression degree of a slide is higher (the numerical value is larger) as the degree of difference from the appearance tendency of the slides in the entirety of the material 20 is larger and the maximum value among the object impression degrees is larger.

The appearance tendency of the slides in the entirety of the material 20 may be determined based on, for example, a ratio among different types of objects included in each of the slides. The ratio among different types of objects may be calculated as, for example, a ratio between the total quantity of image and table objects and the quantity of character string objects, within each of the slides.

In another example, the appearance tendency of the slides in the entirety of the material 20 may be determined based on, for example, how colors are used in each of the slides.

In yet another example, the appearance tendency of the slides in the entirety of the material 20 may be determined based on, for example, positional arrangements of the objects in each of the slides.

In an example, in step S161, the slide impression degree evaluating section 14c may evaluate the slide impression degree of each of the slides based on a degree of simplicity of the slide appearance. In other words, the slide impression degree evaluating section 14c may evaluate the slide impression degree of each of the slides by using a numerical value, by quantifying the degree of simplicity of the slide appearance according to a specific rule. For example, the slide impression degree evaluating section 14c determines such that the slide impression degree of a slide is higher (the numerical value is larger) as the degree of simplicity of the appearance is higher.

The degree of simplicity of the slide appearance may be determined based on, for example, the quantity of objects included in the slide. In other words, the degree of simplicity of the appearance is higher as the quantity of objects is smaller.

In another example, the degree of simplicity of the slide appearance may be determined based on, for example, the total quantity of characters from all the character strings included in each of the slides as objects. In other words, the degree of simplicity of the appearance is higher as the total quantity of characters from all the character strings is smaller.

In yet another example, the degree of simplicity of the slide appearance may be determined based on, for example, positional arrangements of the objects in the slide. For example, a slide having a plurality of objects arranged in bilateral (left/right) symmetry has a higher degree of simplicity of the appearance than a slide having a plurality of objects arranged in bilateral asymmetry. As another example, a slide having an image object arranged at the center thereof has a higher degree of simplicity of the appearance than a slide having an image object arranged in a position other than the center. As yet another example, a slide having a plurality of image objects arranged in regulated positions has a higher degree of simplicity of the appearance than a slide having a plurality of image objects arranged in unregulated positions.

In yet another example, in step S161, the slide impression degree evaluating section 14c may evaluate the slide impression degree of each of the slides, based on a degree of vividness of the colors used in the slide (vividness of the appearance). In other words, the slide impression degree evaluating section 14c may evaluate the slide impression degree of each of the slides by using a numerical value, by quantifying the degree of vividness of the colors used in the slide according to a specific rule. For example, the slide impression degree evaluating section 14c determines such that the slide impression degree of a slide is higher (the numerical value is larger) as the degree of vividness of the colors (the vividness of the appearance) is higher.

The degree of vividness of the colors used in the slide may be determined based on, for example, at least one of the chroma and the brightness of the colors of the objects included in the slide. In other words, the degree of vividness of the colors used in the slide is higher as the chroma of the colors of the objects included in the slide is higher. Also, the degree of vividness of the colors used in the slide is higher as the brightness of the colors of the objects included in the slide is higher.

Alternatively, the degree of vividness of the colors used in the slide may be determined based on, for example, at least one of the chroma and the brightness of the background color of the slide. In other words, the degree of vividness of the colors used in the slide is higher as the chroma of the background color of the slide is higher. Also, the degree of vividness of the colors used in the slide is higher as the brightness of the background color of the slide is higher.

In yet another example, in step S161, the slide impression degree evaluating section 14c may evaluate a slide impression degree of each of the slides comprehensively by using a numerical value, by performing a quantification process on each of all the slides included in the targeted material 20 from each of the various aspects described above and totaling the obtained numerical values in units of slides. In other words, the slide impression degree evaluating section 14c may evaluate the slide impression degree by using the numerical value, by performing the quantification process with respect to two or more aspects selected from the various aspects and adding together the obtained numerical values from those aspects to calculate a total slide impression degree. As described above, the various aspects are: the aspects for determining the appearance tendency of the slides in the entirety of the material 20; the aspects for determining the degree of simplicity of the slide appearance; and the aspects for determining the degree of vividness of the colors used in the slide.

Subsequently, the evaluation displaying section 14b causes the display 12 to display an evaluation result obtained by the slide impression degree evaluating section 14c (step S162). After that, in response of an instruction input via the operating section 11 to end the display of the evaluation result, the controlling section 14 ends the operation shown in FIG. 8.

Figure 9:
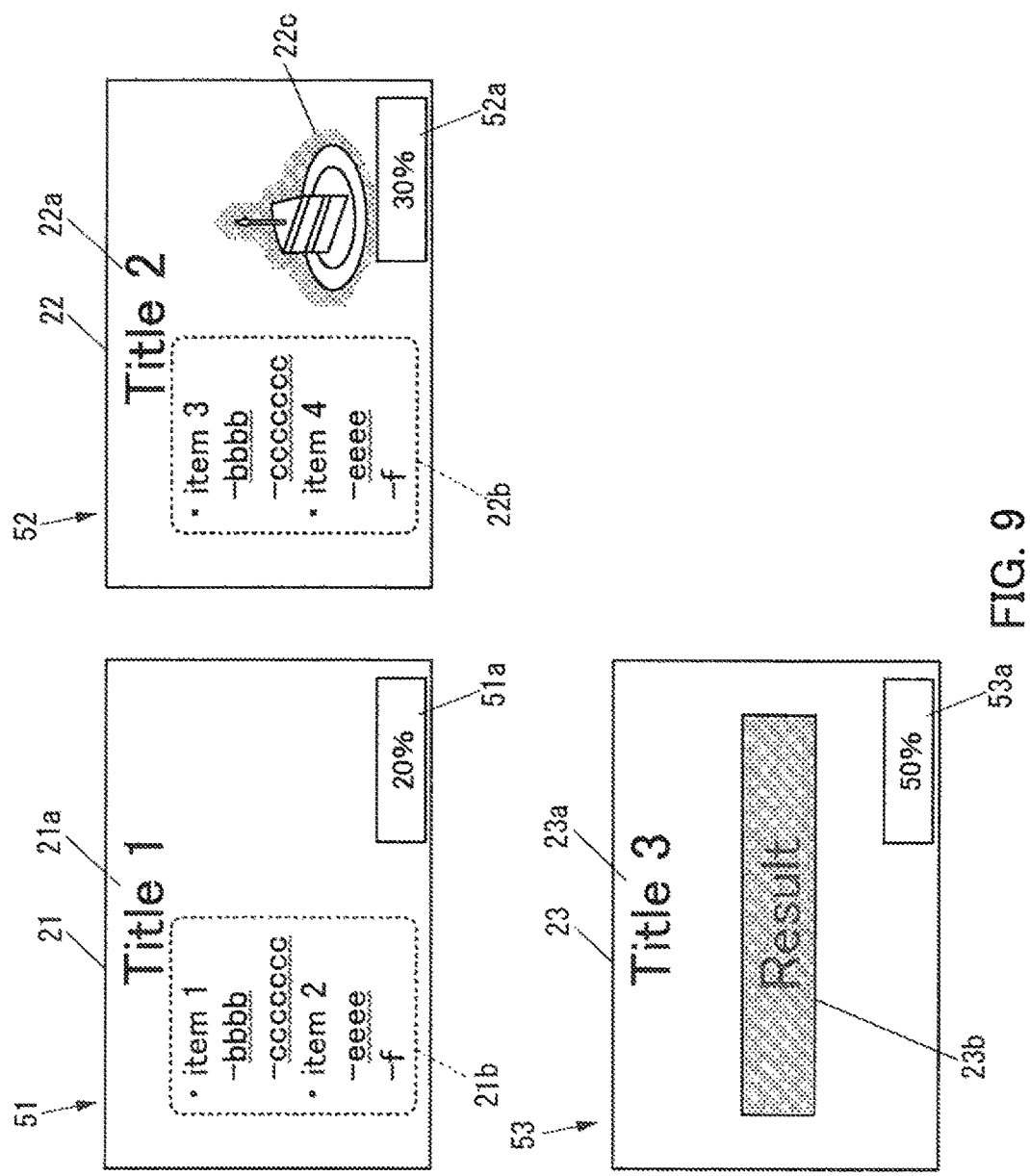
FIG. 9 shows examples of evaluation results about slide impression degrees according to the second embodiment of the present disclosure.

FIG. 9 shows examples of evaluation results about the slide impression degrees displayed on the display 12.

In the evaluation results shown in FIG. 9, an image 51 represents the slide 21. A message 51a indicates 20% as a slide impression degree of the slide 21.

Further, an image 52 represents the slide 22. A message 52a indicates 30% as a slide impression degree of the slide 22.

Further, an image 53 represents the slide 23. A message 53a indicates 50% as a slide impression degree of the slide 23.

The evaluation results shown in FIG. 9 indicate the slide impression degrees with the percentage values, in such a manner that the sum of the slide impression degree values of all the slides included in the material 20 is equal to 100%. However, as long as it is possible to express a relative relationship among the strengths of the impressions made by all the slides included in the material 20, the evaluation results do not necessarily have to be expressed with percentage values. For example, it is acceptable to show the numerical values indicating the slide impression degrees obtained in step S161, without any conversion.

FIG. 9 indicates an example in which the display 12 displays the evaluation results for the three slides at the same time. However, the quantity of slides displayed on the display 12 at the time of an evaluation of the slide impression degrees is not limited to three. For example, the slides may be displayed one by one.

As explained above, the material evaluating apparatus 10 evaluates the slide impression degree of each of all the slides (the slides 21, 22, and 23) included in the material 20 (step S161) and displays the evaluation result (step S162). Accordingly, the material evaluating apparatus 10 is able to help the user objectively recognize which one of the slides in the material 20 makes a strong impression.

In the material 20, a slide having a different appearance tendency from other slides usually makes a strong impression. Thus, the material evaluating apparatus 10 evaluates the slide impression degree of a slide that is significantly different from the appearance tendency of the slides in the entirety of the material 20 as high. As a result, the material evaluating apparatus 10 is able to help the user recognize an appropriate evaluation result.

If one or more objects that make a particularly strong impression are present in a slide having a different appearance tendency from other slides, the slide including the one or more objects that make the particularly strong impression usually makes a particularly strong impression. Thus, if one or more objects that make a particularly strong impression are included in a slide that is significantly different from the appearance tendency of the slides in the entirety of the material 20, the material evaluating apparatus 10 evaluates the slide impression degree of the slide including the one or more objects that make the particularly strong impression as high. As a result, the material evaluating apparatus 10 is able to help the user recognize an appropriate evaluation result.

A simple slide usually makes a strong impression. Thus, when the appearance of a slide is simple, the material evaluating apparatus 10 evaluates the slide impression degree of the slide as high. As a result, the material evaluating apparatus 10 is able to help the user recognize an appropriate evaluation result.

A vivid slide usually makes a strong impression. Thus, when one or more colors used in a slide are vivid, the material evaluating apparatus 10 evaluates the slide impression degree of the slide as high. As a result, the material evaluating apparatus 10 is able to help the user recognize an appropriate evaluation result.

For instance, in the example shown in FIG. 9, the appearance of the slide 23 is significantly different from the appearance tendency of the slides 21 and 22. In addition, the appearance of the slide 23 is simple, while the color used for the object 23b is vivid. As a result, among the slides 21, 22, and 23 shown in FIG. 9, the slide impression degree of the slide 23 is evaluated as the highest. Further, because the slide 22 includes the image object 22c having a high object impression degree, the slide impression degree of the slide 22 is evaluated as higher than that of the slide 21.

The material evaluating apparatus 10 is not only able to evaluate the slide impression degree of each of all the slides included in the material 20 (step S161) and to display the evaluation result (step S162), but is also able to evaluate the object impression degree for each of all the objects included in the slides and to display the evaluation result. Thus, the material evaluating apparatus 10 is able to help the user objectively recognize which object in which slide in the material 20 makes a strong impression.

By acknowledging the objective evaluation results about the slide impression degrees and the object impression degrees displayed by the material evaluating apparatus 10, the creator of the material 20 is able to objectively recognize if a part of the material 20 where he/she desires the impression to be strong makes a strong impression as desired. As a result, the creator of the material 20 is able to appropriately revise the material 20 in a short period of time.

What is claimed is:

1. A non-transitory computer-readable storage medium that has stored therein a material evaluating program to be executed by a computer, the material evaluating program comprising:
    a first program code that causes the computer to evaluate, in units of pages included in a material, an object impression degree for each of all objects included in each of the pages, the object impression degree indicating a strength of an impression made by the object included in the page;
    a second program code that causes the computer to display a first evaluation result obtained by executing the first program code;
    a third program code that causes the computer to detect a plurality of pages belonging to the same group from the material through the computer determining that the plurality of pages from which objects of the same type are detected belong to the same group;
    a fourth program code that causes the computer to evaluate uniformity of the plurality of pages belonging to the same group and detected by executing the third program code based on each of the following aspects: positions of the objects of the same type included in the respective plurality of pages belonging to the same group; sizes of the objects of the same type included in the respective plurality of pages belonging to the same group; colors of the objects of the same type included in the respective plurality of pages belonging to the same group; and background colors of the respective plurality of pages belonging to the same group;
    a fifth program code that cause the computer to determine for each of the aspects whether or not a numerical value indicating the uniformity is equal to or larger than a first specific value;
    a sixth program code that causes the compute to classify the plurality of pages belonging to the same group into a plurality of categories based on the numerical value indicating the uniformity for any of the aspects for which it is determined that the numerical value indicating the uniformity is equal to or larger than the first specific value;
    a seventh program code that causes the computer to determine for any of the aspects for which it is determined that the numerical value indicating the uniformity is equal to or larger than the first specific value whether or not a difference in quantity of pages of each of the classified types is equal to or larger than a second specific value; and
    an eighth program code that causes the computer to display an evaluation result of the uniformity when it is determined that the difference in quantity of the pages of each of the classified types is equal to or larger than the second specific value.

2. A non-transitory computer-readable storage medium according to claim 1, wherein
    the first program code causes the computer to evaluate each of the object impression degrees based on at least one of the following: a type of the object; a position of the object in the page; a size of the object; color differences among all the objects; a color difference between the object and a background of the page; a text size of a character string when the type of the object is a character string; and a quantity of characters in a character string when the type of the object is a character string.

3. A non-transitory computer-readable storage medium according to claim 2, wherein
    the first program code causes the computer to arrange the object impression degree to be higher as a magnitude of the color difference between the object and the background of the page is larger.

4. A non-transitory computer-readable storage medium according to claim 2, wherein
    the first program code causes the computer to arrange the object impression degree to be higher as a sum of magnitudes of color differences between the object and all the other objects is larger.

5. A non-transitory computer-readable storage medium according to claim 2, wherein
    the first program code causes the computer to arrange the object impression degree of an object of which the type is an image to be higher than the object impression degree of an object of which the type is a character string.

6. A non-transitory computer-readable storage medium according to claim 1, wherein
    the material evaluating program further comprising a ninth program code that causes the computer to evaluate a page impression degree for each of all the pages included in the material, the page impression degree indicating a strength of an impression made by the page included in the material, and the second program code causes the computer to display a third evaluation result obtained by executing the ninth program code.

7. A non-transitory computer-readable storage medium according to claim 6, wherein the ninth program code causes the computer to arrange the page impression degree of the page to be higher as a degree of difference in an appearance of the page from an appearance tendency of all the pages is higher.

8. A non-transitory computer-readable storage medium according to claim 6, wherein the ninth program code causes the computer to arrange the page impression degree of the page to be higher as a maximum value among the object impression degrees within the page is larger.

9. A non-transitory computer-readable storage medium according to claim 6, wherein the ninth program code causes the computer to arrange the page impression degree of the page to be higher as a degree of simplicity of an appearance of the page is higher.

10. A non-transitory computer-readable storage medium according to claim 6, wherein the ninth program code causes the computer to arrange the page impression degree of the page to be higher as a degree of vividness of one or more colors used in the page is higher.

11. The non-transitory computer-readable storage medium according to claim 1, wherein in evaluation of the uniformity of the plurality of pages belonging to the same group based on the aspect of background colors of the respective plurality of pages belonging to the same group, that the numerical value indicating the uniformity is equal to or larger than the first specific value indicates that plural types of background colors are present and classification of the plurality of pages belonging to the same group indicates division of the plurality of pages for each of the background colors.

12. A material evaluating apparatus comprising:

a display; and a processor that executes a material evaluating program, wherein through execution of the material evaluating program, the processor functions as:

an object impression degree evaluating section that evaluates, in units of pages included in a material, an object impression degree for each of all objects included in each of the pages, the object impression degree indicating a strength of an impression made by the object included in the page;

a first evaluation displaying section that causes the display to display a first evaluation result obtained by the object impression degree evaluating section;

a detecting section that detects a plurality of pages belonging to the same group from the material through determination that the plurality of pages from which objects of the same type are detected belong to the same group;

a uniformity evaluating section that evaluates uniformity of the plurality of pages belonging to the same group and detected by the detecting section based on each of the following aspects: positions of the objects of the same type included in the respective plurality of pages belonging to the same group; sizes of the objects of the same type included in the respective plurality of pages belonging to the same group; colors of the objects of the same type included in the respective plurality of pages belonging to the same group; and background colors of the respective plurality of pages belonging to the same group;

a first determining section that determines for each of the aspects whether or not a numerical value indicating the uniformity is equal to or larger than a first specific value;

a classifying section that classifies the plurality of pages belonging to the same group into a plurality of categories based on the numerical value indicating the uniformity for any of the aspects for which it is determined that the numerical value indicating the uniformity is equal to or larger than the first specific value;

a second determining section that determines for any of the aspects for which it is determined that the numerical value indicating the uniformity is equal to or larger than the first specific value whether or not a difference in quantity of pages of each of the classified types is equal to or larger than a second specific value; and a second evaluation section that causes the display to display an evaluation result of the uniformity when it is determined that the difference in quantity of the pages of each of the classified types is equal to or larger than the second specific value.

13. A material evaluating apparatus according to claim 12, wherein through execution of the material evaluating program, the processor further functions as a page impression degree evaluating section that evaluates a page impression degree for each of all the pages included in the material, the page impression degree indicating a strength of an impression made by the page included in the material, and the evaluation displaying section further causes the display to display a third evaluation result obtained by the page impression degree evaluating section.

14. The material evaluating apparatus according to claim 12, wherein when the uniformity evaluating section evaluates the uniformity of the plurality of pages belonging to the same group based on the aspect of background colors of the respective plurality of pages belonging to the same group, that the numerical value indicating the uniformity is equal to or larger than the first specific value indicates that plural types of background colors are present and classification of the plurality of pages belonging to the same group indicates division of the plurality of pages for each of the background colors.

15. A material evaluating method performed by a processor through execution of a material evaluating program, the material valuating method comprising:

evaluating, by the processor and in units of pages included in a material, an object impression degree for each of all objects included in each of the pages, the object impression degree indicating a strength of an impression made by the object included in the page;

displaying by the processor a first evaluation result obtained by evaluating the object impression degree;

detecting by the processor a plurality of pages belonging to the same group from the material through the processor determining that the plurality of pages from which objects of the same type are detected belong to the same group;

evaluating by the processor uniformity of the plurality of pages belonging to the same group based on each of the following aspects: positions of the objects of the same type included in the respective plurality of pages belonging to the same group; sizes of the objects of the same type included in the respective plurality of pages belonging to the same group; colors of the objects of the same type included in the respective plurality of pages belonging to the same group; and background colors of the respective plurality of pages belonging to the same group;

determining by the processor for each of the aspects whether or not a difference in quantity of pages of each of the classified types is equal to or larger than a second specific value; and classifying by the processor the plurality of pages belonging to the same group into a plurality of categories based on the numerical value indicating the uniformity for any of the aspects for which it is determined that the numerical value indicating the uniformity is equal to or larger than the first specific value;

determining by the processor for any of the aspects for which it is determined that the numerical value indicating the uniformity is equal to or larger than the first specific value whether or not a difference in quantity of pages of each of the classified types is equal to or larger than a second specific value; and displaying by the processor an evaluation result of the uniformity when it is determined that the difference in quantity of the pages of each of the classified types is equal to or larger than the second specific value.

16. A material evaluating method according to claim 15, further comprising:

evaluating by the processor a page impression degree for each of all the pages included in the material, the page impression degree indicating a strength of an impression made by the page included in the material; and displaying by the processor a third evaluation result obtained by evaluating the page impression degree.

17. The material evaluating method according to claim 15, wherein when the processor performs the evaluating the uniformity of the plurality of pages belonging to the same group based on the aspect of background colors of the respective plurality of pages belonging to the same group, that the numerical value indicating the uniformity is equal to or larger than the first specific value indicates that plural types of background colors are present and classification of the plurality of pages belonging to the same group indicates division of the plurality of pages for each of the background colors.

* * * * *